United States Patent
Hamill et al.

(10) Patent No.: US 11,424,010 B2
(45) Date of Patent: Aug. 23, 2022

(54) METHOD FOR MINIMIZING ENTRY OF MEDICALLY SIMILAR ORDERS IN A COMPUTERIZED MEDICAL RECORDS SYSTEM

(71) Applicant: Epic Systems Corporation, Verona, WI (US)

(72) Inventors: Aaron Hamill, Madison, WI (US); Mandi Stevens, Madison, WI (US); Christopher Alban, Madison, WI (US); Bradley C. Eichhorst, Verona, WI (US); Sam Frymark, Madison, WI (US)

(73) Assignee: Epic Systems Corporation, Verona, WI (US)

( * ) Notice: Subject to any disclaimer, the term of this patent is extended or adjusted under 35 U.S.C. 154(b) by 855 days.

(21) Appl. No.: 15/677,594

(22) Filed: Aug. 15, 2017

(65) Prior Publication Data

US 2017/0344705 A1 Nov. 30, 2017

Related U.S. Application Data (63) Continuation of application No. 14/150,387, filed on Jan. 8, 2014, now abandoned.

(60) Provisional application No. 61/753,161, filed on Jan. 16, 2013.

(51) Int. Cl.
*G16H 10/60* (2018.01)

(52) U.S. Cl.
CPC .................... *G16H 10/60* (2018.01)

(58) Field of Classification Search
USPC ........................................................ 705/2–4
See application file for complete search history.

(56) References Cited

U.S. PATENT DOCUMENTS

| | | | | |
|---|---|---|---|---|
| 6,125,350 A * | 9/2000 | Dirbas | ................... | G16H 10/60 705/2 |
| 8,548,824 B1 * | 10/2013 | daCosta | ................ | G16H 20/13 705/3 |
| 2004/0010425 A1 * | 1/2004 | Wilkes | ................... | G16H 40/20 705/3 |
| 2007/0055550 A1 * | 3/2007 | Courtney | ............... | G06Q 50/24 705/3 |
| 2008/0255883 A1 * | 10/2008 | Jones | ..................... | G06Q 10/10 705/3 |
| 2009/0048864 A1 * | 2/2009 | Kozlowski | ............. | G06Q 10/10 705/2 |
| 2011/0077954 A1 * | 3/2011 | Schneider | ............. | G06F 19/325 705/2 |
| 2011/0184755 A1 * | 7/2011 | Yamaga | ................. | G16H 20/10 705/3 |
| 2014/0200921 A1 * | 7/2014 | Hamill | ................... | G16H 10/60 705/3 |

* cited by examiner

*Primary Examiner* — Mark Holcomb
(74) *Attorney, Agent, or Firm* — Quarles & Brady, LLP (57) ABSTRACT

An electronic medical records system with computerized provider order entry includes error checking for duplicate or medically similar orders. In the system, similar medical orders are displayed on adjacent screens and are highlighted, thereby allowing medical personnel to easily identify and evaluate the orders. The user can therefore choose to modify or delete medically similar entries easily and quickly, thereby minimizing the occurrence of duplicate or repetitive orders, and increasing efficiency of the system.

25 Claims, 9 Drawing Sheets

| PATIENT IDENTIFICATION | PATIENT MEDICAL ORDER | | ORDER TYPE | EXISTING ORDERS | PROBLEMS |
|---|---|---|---|---|---|
| JOHN SMITH 1234 MAPLE LANE HOMETOWN, IA | ALLERGIES | LATEX BEE VENOM PENICILLIN | LABS | BASIC METABOLIC PANEL | VISION BLURRING |
| | | | | ELECTROLYTES | HIGH CHOLESTEROL |
| | PRESCRIPTIONS | ATORVASTATIN (LIPITOR) 10MG | | FINGERSTICK GLUCOSE | ARTHRITIS, RHEUMATOID |
| | | ETANERCEPT (ENBREL) 50MG | IMAGING | X-RAY ABDOMEN | GERD (GASTROESOPHAGEAL REFLUX DISEASE) |
| | | RANITIDINE (ZANTAC) 75MG | | X-RAY CHEST | |
| | | | MEDICATION ORDER – PRN | ACETAMINOPHEN LORAZEPAM | |

METHOD FOR MINIMIZING ENTRY OF MEDICALLY SIMILAR ORDERS IN A COMPUTERIZED MEDICAL RECORDS SYSTEM

CROSS-REFERENCE TO RELATED APPLICATIONS

This application is a continuation of U.S. patent application Ser. No. 14/150,387 filed Jan. 8, 2014, and claims priority to U.S. Provisional Application Ser. No. 61/753,161 filed Jan. 16, 2013, each of which is hereby incorporated by reference in its entirety.

BACKGROUND OF THE INVENTION

In recent years, rising health care costs have led to an increased emphasis on computerization of health care, and particularly the development and use of electronic medical records (EMR) and computerized provider order entry (CPOE). Electronic medical records and computerized provider order entry provide many advantages over prior art paper medical record documentation systems. Moving from paper to electronic records and orders can, for example, increase the efficiency of health care, as well as health and insurance payment systems.

Electronic medical records and orders also provide an important advantage because they simplify both the storage and transfer of important medical history data, including prescribed drugs, blood type, allergies, and existing medical conditions, and enable electronic verification and checking of data. Electronic medical records are typically also more complete than the medical records of the past, which often relied on information retrieved directly from the patient. The patient data could be incomplete due to memory failure, or the failure to maintain complete personal records. Computerized medical systems, therefore, are an important improvement over prior art processes and lead to improved diagnosis and treatment decisions.

While computerized medical systems and records provide important improvements in patient care and help to reduce health care costs the ease of entry of medical data in computerized systems can also lead to some problems. The online journal of the American Medical Informatics Association, for example, recently published an article evaluating the incidence of duplicate medication orders before and after computerized provider order entry. This study found that the ease of order entry actually increased the number of duplicative order errors at studied hospitals, and that the entry of duplicative orders had more than tripled after the introduction of CPOE—increasing from 2.6% to 8.1%. Because duplicate orders can lead to unnecessary and costly duplication of medical procedures, decrease efficiency by tying up resources that could be used elsewhere, and adversely impact inventory procedure in pharmacies and other areas of medical facilities, it is important to minimize duplicate, similar, and overlapping entries.

Existing medical order systems often use pop-up windows to notify the medical practitioner that a duplicate or similar order exists. While these warnings can be effective in some cases, pop-up windows are often easy to disable, and are frequently ignored by computer users, who suffer from "fatigue" due to over-use of pop-up windows, or who associate pop-up windows with unwanted advertising. These systems, therefore, are often ineffective, and do not minimize duplicative order entry by medical personnel.

The present invention addresses these and other issues.

SUMMARY OF THE INVENTION

In one aspect, the present invention can provide a medical records computer system that includes a processor, a memory coupled to the processor and storing a patient database, a user interface device coupled to the processor, and a display communicatively coupled to the processor and the memory. The display includes an existing order portion displaying at least one existing medical order retrieved from the patient database, and a new order portion adjacent the existing order portion for displaying a new medical order entered by medical personnel using the user interface. The processor is programmed to receive and display the new medical order on the new order portion of the display, compare the new medical order to the existing medical orders in the patient database to determine whether the existing medical order is medically similar to the new medical order, and highlight at least one of the existing medical order and the new medical order on the display when the existing medical order is medically similar to the new medical order. A medical practitioner entering the new order, therefore, is provided with a warning in real time to prevent the entry of a medically similar order, and therefore to minimize the possibility of the entry of medically similar orders for the patient.

The existing order portion of the display can display a plurality of existing medical orders categorized in medical order types. The processor can also be programmed to highlight the medical order type that contains the existing medical order that is medically similar to the new order. Again, the medical practitioner is therefore notified of the existing orders for quick analysis without the need for a pop-up window or display.

The processor can also be programmed to highlight at least one of the existing medical order and the new medical order on the display by changing a font of at least one of the existing medical order and the new medical order, by changing a color of the font, or by applying a color highlight to at least one of the existing medical order and the new medical order on the display. The processor can also or alternatively be programmed to highlight at least one of the existing medical order and the new order on the display by visually enclosing the selected order within a line or box on the display.

The processor can also be programmed to scroll the display to position the existing medical order and the new medical order adjacent one another in the first and second portions of the display, or to sort the existing medical orders to position an identified existing medical order at a position adjacent the medically similar new medical order.

The medical records computer system can also include a database storing a plurality of known medical orders and similar medical orders, and the processor can be programmed to compare the known medical orders to the new medical order to identify a match, retrieve the corresponding similar medical orders from the database, compare the similar medical orders to the existing medical order to determine whether the new medical order is similar to the existing medical order, and highlight the existing medical order when it is similar to the new medical order. The database can also correlate the known medical orders with categories of medical order types, and the existing medical orders can be correlated with corresponding medical order types on the display. The processor can be further programmed to highlight the medical order type corresponding to the new medical order on the existing order portion of the display.

The medical records system can include a memory storing a medical orders database comprising a plurality of known medical orders grouped in a plurality of categories based on a medical order type, and a patient database comprising at least one existing medical order initiated for a selected patient which is also categorized in a medical order type and can compare the new medical order to the orders database to determine a medical order type. The processor can also compare the new medical order to the existing medical orders of the same medical order type in the patient database to determine whether the existing medical order is medically similar to the new medical order, and highlight at least one of the existing medical order type corresponding to the new medical order, the existing medical order that is medically similar to the new medical order, and the new medical order on the display when the existing medical order is medically similar to the new medical order. Again, the medical practitioner entering the new order is provided with a warning in real time to prevent the entry of a medically similar order.

The existing order portion of the display can display a plurality of existing medical orders categorized in medical order types, and the processor can be programmed to highlight at least one of the predetermined medical order types that contains the existing medical order that is medically similar to the new order.

The processor can also be programmed to group the existing medical order with other existing medical orders of the same medical order type on the display, and to highlight the medical order type that corresponds to the new medical order in the existing order portion of the display when a similar or duplicate order is found. In some applications, the processor can also be programmed to scroll the medical order type corresponding to the new medical order to a top portion of the existing order portion of the display to highlight the duplicate or similar entry.

The processor can also be programmed to visually group the existing medical orders corresponding to a medical order type by enclosing the existing medical orders in a box in the existing order portion of the display or to highlight at least one of the existing medical order and the new medical order on the display by scrolling the display to position the existing medical order and the new medical order adjacent one another in the first and second portions of the display, or by sorting the existing medical orders to position the existing medical order at a position adjacent the new medical order, or to highlight existing medical orders of the same medical order type to the new order to allow a medical practitioner to compare the new medical order to existing medical orders.

In another aspect, the present invention can comprise a method for minimizing entries of duplicate medical orders by medical personnel in a computerized medical records system. The method comprises the steps of storing at least one existing medical order initiated by medical personnel for a specific patient, and displaying the existing medical order on a first portion of a display screen, receiving a new medical order for the patient through a user interface, and displaying the new medical order on a second portion of a display screen. A processor compares the new medical order to the existing medical order, and highlights at least one of the existing medical order and the new medical order to provide a real time notification that at least one of a similar and a duplicate order has been entered.

To identify similar orders, the method can also include storing a plurality of known medical orders and similar medical orders in a database for comparison, comparing the known medical orders to the new medical order to identify a match, retrieving the corresponding similar medical orders, comparing the similar medical orders to the existing medical order to determine whether the new medical order is similar to the existing medical order, and highlighting the existing medical order when it is similar to the new medical order.

The method can also include categorizing each of the existing medical orders as a predetermined medical order type, determining the medical order type of the new medical order, and highlighting the corresponding medical order type in the first portion of the display to enable a user to identify a duplicate or similar order. The method can further comprise the steps of comparing the new medical order to a database of known medical orders, and providing a warning to the user when a spelling error is detected. The user can also be provided with one or more alternatives for the user to select when the new medical order does not match any of the known medical orders.

These and other aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefore, to the claims herein for interpreting the scope of the invention.

DETAILED DESCRIPTION OF THE INVENTION

Figure 1:
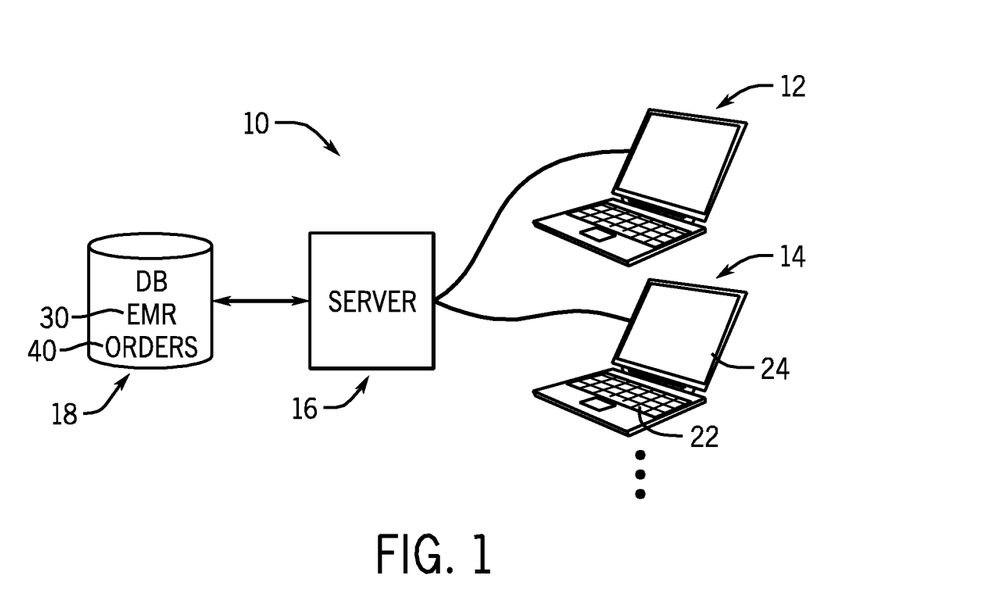
FIG. 1 is block diagram of a computerized health care information system for use with the present invention.

Referring now to the figures, and more particularly to FIG. 1, a typical computerized medical records system 10 on which the present invention can be used is shown. The medical records computer system 10, as shown here, comprises a central computer or server 16, and a memory storage device 18 which stores databases of electronic medical records 30 (EMR) and medical orders 40. The server 16 can be accessed by medical personnel through terminals or computers 12 and 14 in communication with the server 16 at an inpatient facility, such as a hospital, clinic, or rehabilitation center, or at an outpatient facility. During an examination or patient visit, medical personnel access the electronic medical record for the patient by accessing the database 30 through the computer 12 or 14. The data retrieved includes existing orders for the patient. When a new medical order is initiated by medical personnel, the system compares the new order against existing medical orders and data in the medical orders database 40, and provides an indicator to the medical personnel if a medically similar order exists, thereby minimizing occurrences of medically similar orders, as described below. As used herein, the term "medically similar" means an order that is either duplicative of, therapeutically or diagnostically overlapping of, or therapeutically and/or diagnostically similar to an existing order. Medically similar orders can include, for example, different medications that are commonly ordered as a treatment for the same condition, or to treat the same symptoms, and which may therefore be effective duplicates. Similar medications can be identified as therapeutically or diagnostically similar, for example, based on their current procedural terminology (CPT) codes, including ICD-9 and ICD-10 coding. Here, medications in the same therapeutic class, and orders that are numerically similar in CPT code may overlap in treatment. Also, in some cases, a single lab order includes results that can also be obtained by taking a number of individual lab tests. A complete blood count (CBC), for example, includes a white blood cell (WBC) count. A WBC, therefore, overlaps an existing CBC order, as well as CBC with differential, CBC without differential, and CBC manual differential tests. Imaging procedures which acquire duplicate images of the same sector of the patient can also be duplicative.

Figure 2:
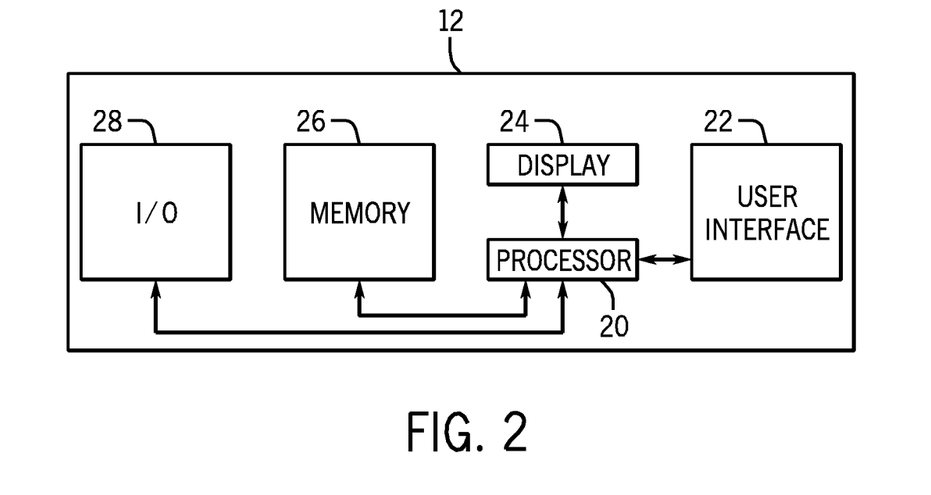
FIG. 2 is a block diagram of a computer or other computerized device for providing access to the computerized health care information system of FIG. 1.

Referring still to FIG. 1 and also to FIG. 2, each of the computers 12 and 14 comprises a user interface 22 for entry of data by medical personnel, and a display 24. The computing devices 12 and 14 can comprise any number of known devices that are connectable to a network, and can include, without limitation, personal computing devices, cellular phones, tablets, notebooks, laptops, desktop computers, all-in-one computers, and other types of computer configurations. The computing devices 12 and 14 can be connected to the server 16 through the internet, or through other public or private networks including wide area networks, local area networks, wireless interfaces, cellular communication links, satellite communications, and various other types of communication links which will be known to those of ordinary skill in the art. Although the computer is shown here in a network configuration, stand alone computer devices capable of maintaining or connecting to appropriate databases can also be used without the need for a server or network.

Referring now to FIG. 2, an exemplary computer system 12 or 14 is shown. The computers 12 and 14, as described above, include a display 24 and a user interface 22, which are communicatively coupled to an internal processor 20, memory 26, and a communications or input/output (I/O) device 28 which can, as described above, link the computing device 12 to a server 16 or other external devices. As shown in FIG. 1, the user interface 22 can be or include a keyboard, mouse, joystick, pen, or other devices capable of providing input to the computer 12. Alternatively, the display 24 can be provided with a touch screen, and the user interface 22 can be configured as a portion of the display function. The user interface 22 or the I/O device 28 can also include cameras and scanning devices, including magnetic, optical, or barcode scanners, and data ports such as universal serial bus (USB), RS-232, or other types of wired and wireless data links. Selective access can be provided to the system using password protection, biometric data, retinal scanners, fingerprint scanners, vascular biometrics analyzing the back of the hand or finger vein scans, RFID readers, encoded digital symbols such as bar codes, and other types of identifiers and reader devices. The computers 12 and 14 may also include audio generation systems and speakers, which are not shown.

Figure 3:
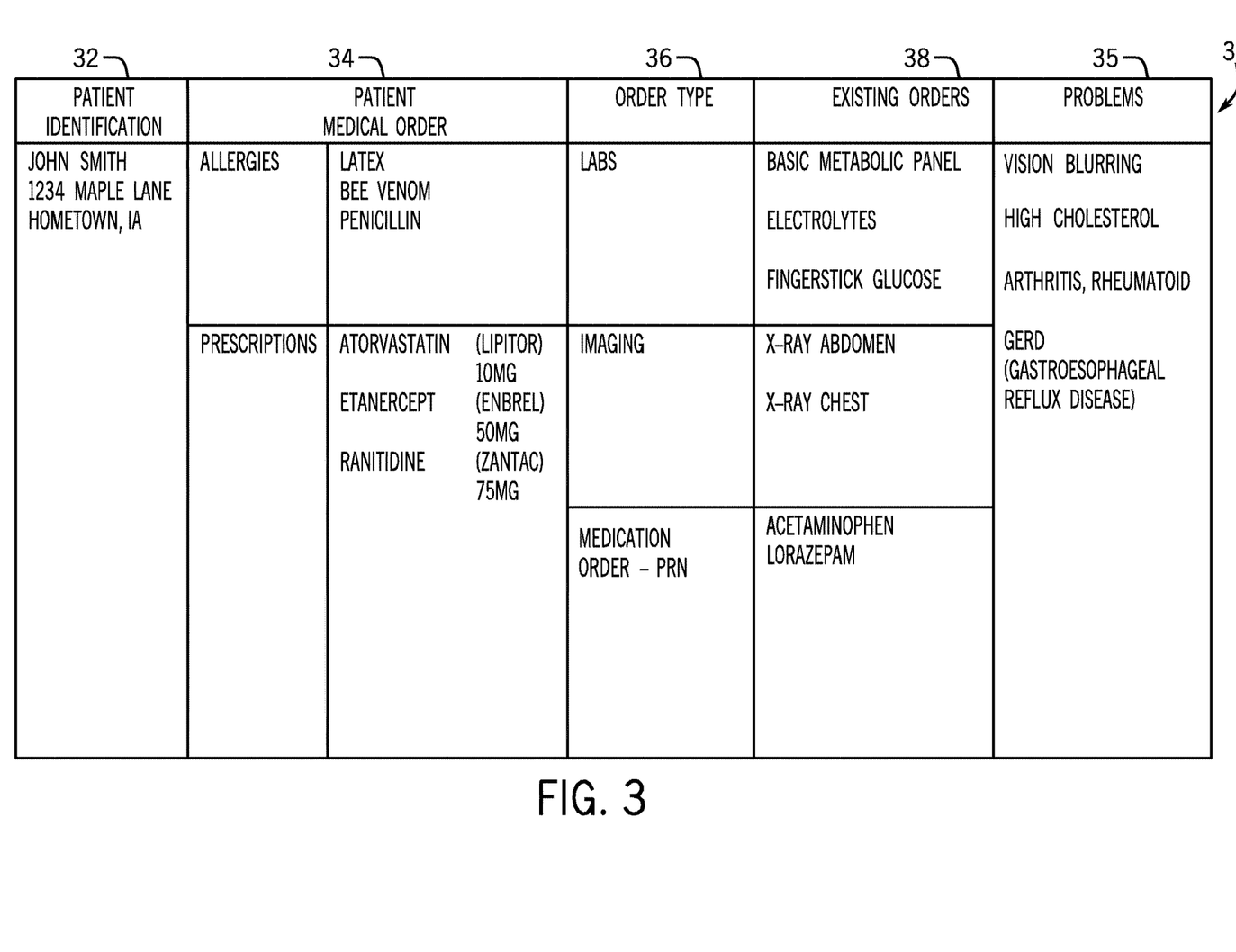
FIG. 3 is an illustration of an exemplary patient records database for use in accordance with the system of the present invention.

Referring now to FIG. 3, an exemplary EMR database 30 includes electronic medical records for patients, as described above. The database can include a patient identifier 32, patient medical data 34, medical order types 36, and corresponding data related to existing medical orders 38 that have been entered for the patient. As shown here, the patient identification data can include a name and address of a patient, and may also include alternative identifiers such as social security number, insurance information and/or finger print, retinal scan, or other types of personal identification data or codes. Also as shown here, the patient medical data 34 can include information that can be used by medical personnel to identify drugs which are not appropriate for a given patient, including information about the patient's allergies (latex, bee venom, and penicillin) and information about medication orders the patient is already taking.

Medical order types 36 can include for instance, a request from medical personnel for an inpatient or outpatient procedure, a medication, a laboratory test, an evaluation, a treatment, or a nursing task to be performed. As used herein, medical order types can also include, for example, laboratory orders, imaging orders, diet, consults, and other types of orders made by medical personnel for a patient. Medication orders can also include, for example, medications taken at home by a patient including take-home medications, discharge medications, prescriptions, and facility administered medications including persistent facility-administered medications and prescriptions. For purposes of identifying similar or duplicate orders, medication orders can be divided into specified sub-types of Medical Orders 36 such as, for example, medication order—pro re nata (PRN or "as needed" medication orders), medication order—continuous, and medication order—scheduled pharmaceutical delivery.

Referring still to FIG. 3, existing medical orders 38 are correlated with medical order types 36, and can be categorized to correspond to one or more medical order type 36. In applications where CPT coding is used, for example, medical orders 38 within a predetermined numerical range of the CPT code assigned to the medical order 38 can be presumed to be medically similar. In these applications, the medical order type can correspond to a numerical range of CPT codes, and can be provided in the database 30 corresponding to the medical order 38 to provide a range for searching for medically similar orders. More generally, a medical order 38 may require a patient to take a medication prior to a blood test or other laboratory analysis. Here, the medical order 38 therefore can be appropriately categorized as both a lab order and a medication order for purposes of identifying a medical order type 36 and medically similar orders. The degree or level of similarity can be used to prioritize medical orders 36 with the corresponding medical order types 38 in database 30 and for comparison purposes.

Referring still to FIGS. 2 and 3, when a medical practitioner evaluates the patient to initiate additional orders, new orders for the patient can be entered into a window on display 22 as described more fully below. The entered data can be evaluated to determine whether the newly initiated order is medically similar to an existing order 38.

Figure 4:
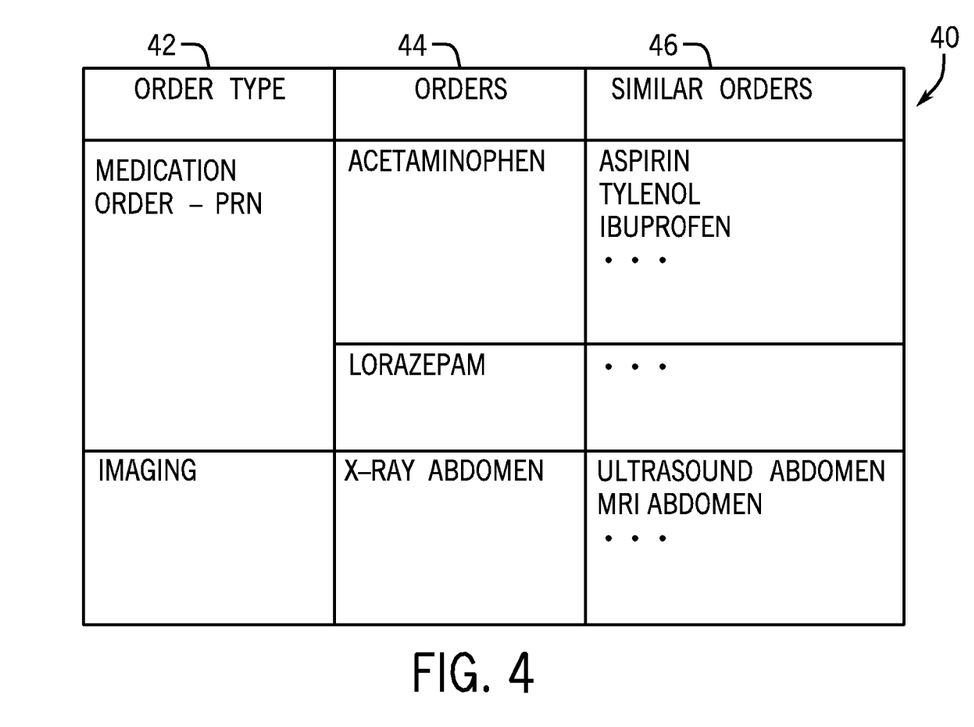
FIG. 4 is an illustration of an exemplary medical orders database for use in accordance with the system of the present invention.

Referring now to FIG. 4, one method of providing this function is by comparison to a medical orders database 40. The medical orders database 40 can include a listing of known medical orders, including a standardized listing of medical order types 42, specific medical orders 44 that correlate to the medical order type, and also, a list of medically similar orders 46 that are pre-determined to be sufficiently medically similar to the corresponding order to require a notification to medical personnel that the order may be unnecessary or unduly repetitive. The medical orders database 40 can be constructed specifically for a hospital, clinic, or other facility, or can be based on standards from public databases. Standard medical data can, for example, be retrieved through the internet or other networks and can be, as described above, CPT coding. Also as described above, the medical orders 44 can correspond to one or more medical order type 42. Again, the corresponding medical order types 42 can be prioritized, or a degree of similarity to the corresponding medical order types 42 can be stored in memory with the medical orders 44. Also as discussed above, where CPT coding is used, it can be assumed that CPT codes that are within a predetermined numerical range of the CPT code corresponding to the medical order 44 may be medically similar. Although a specialized medical orders database is shown here, standardized CPT codes and IC-9 and IC-10 databases can be accessed to provide similar types of data.

Figure 5:
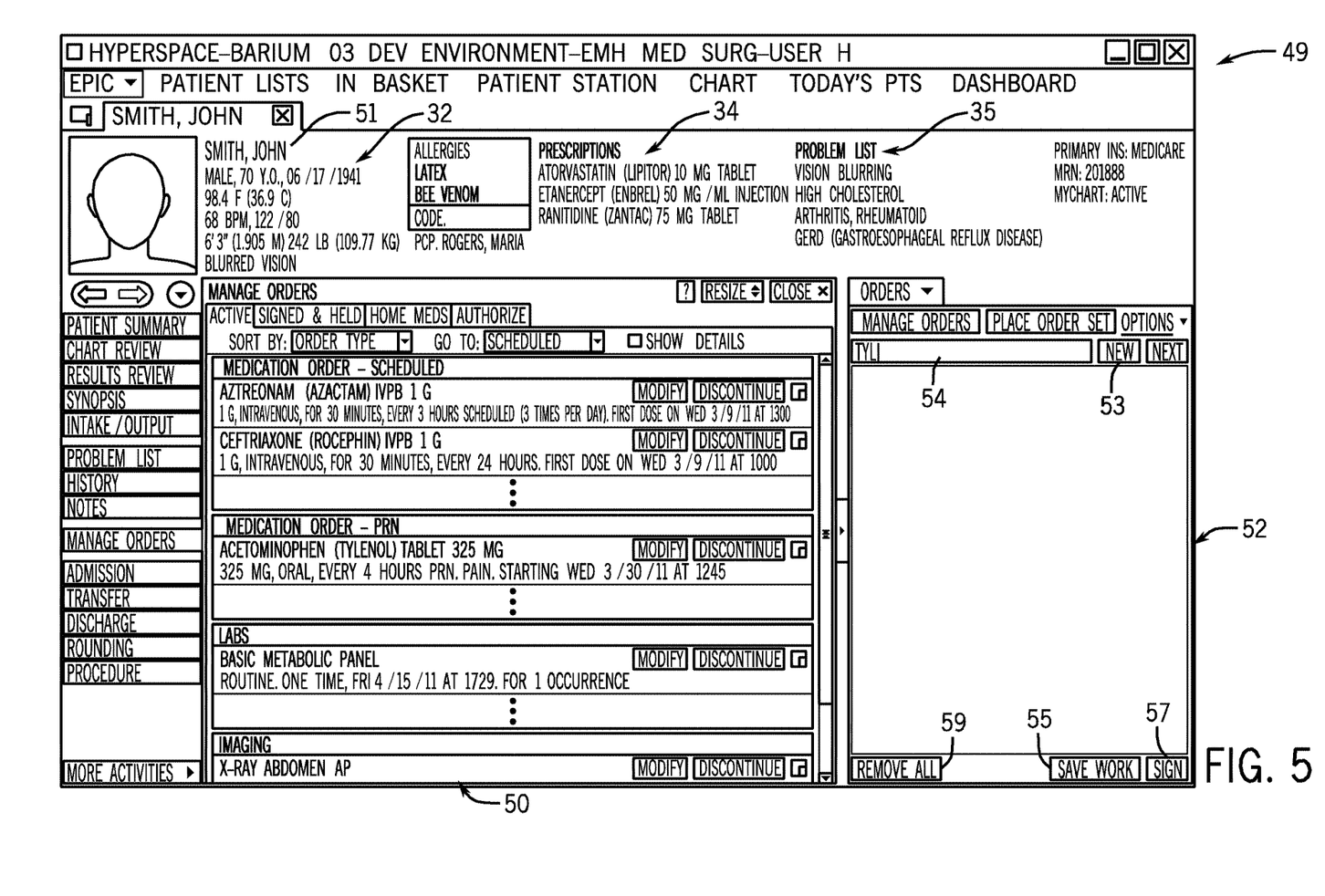
FIG. 5 is an illustration of an exemplary screen for medical order data entry and comparison prior to entry of a new medical order.

Referring now to FIG. 5, an exemplary display screen 49 for use by a medical practitioner is shown. The display screen 49 is provided on display 22 of computer 12 (FIG. 1) and can include a plurality of sections or windows, including an existing order section 50 for displaying existing orders 38 for the patient from database 30, and a new order entry section 52 for entering or editing medical orders. A patient data section 51 can also be included. In one embodiment, as shown here, the patient data section 51 can be provided along an upper portion of the screen 49, and the existing order section 50 and new order entry section 52 adjacent one another, where the existing order data can be viewed by a medical practitioner simultaneously with the new order data, as the data is entered into the order entry section 52 of the screen 49. As shown here, the existing order section 50 and order entry section 52 can be in two adjacent columns.

Referring still to FIG. 5, the patient data section 51 displays information from patient database 30 and can include patient identification data 32, such as a name, address, physical description, and a picture of the patient for verification by medical practitioners, and other data drawn from the database 30, to allow a medical practitioner easy access to verify identification of the patient. The display screen 49 can also illustrate patient medical data 34 derived from database 30 for use by medical personnel in evaluating whether a specific type of order may be appropriate for the patient. This data can include, as described above, blood type information, patient allergy data, and important medical history data. The patient data can also include a list of identified medical problems for analysis and diagnosis.

Referring still to FIG. 5 and also to FIG. 3, the existing medical order section 50 displays each of the existing orders 38 that have been previously entered for the patient, which can be retrieved from the database 30, along with icons that can be selectively activated by a medical practitioner to modify or discontinue the order. The existing orders are categorized by medical order type 36, and all of the existing orders 38 of a particular type are grouped together on the screen 49 in the existing order section 50. The grouped medical orders can include a visual indicator grouping all of the existing medical orders 38 of the same medical order type 42 together, as discussed below.

Referring still to FIG. 5, after examining the patient, the medical practitioner can enter new medical orders into the order entry section 52 of the screen 49. As shown here, the new order section 52 can include, for example, a text box section or window 54 that accepts input from the user interface 22. A medical practitioner enters the new medical order into the text box 54. As described below, as and after the text is entered into the text box 54, the processor 20 takes a series of steps to evaluate whether medically similar orders have already been entered for the patient, and highlights any identified similar orders to notify the medical practitioner of a potential problem. A sequence diagram illustrating these steps is shown at FIG. 10. Generally, the process begins by clearing the old highlights (step 69). After new orders are entered (step 70), the new orders are highlighted in a sidebar or window, the new order section 52 (step 76). As described more fully below with reference to FIG. 9, corresponding groups of existing medical orders 38 having the same medical order type 36 are highlighted (step 79) in the existing order section 50 and then the existing orders 36 that are medically similar to the new order are highlighted (step 82).

Figure 6:
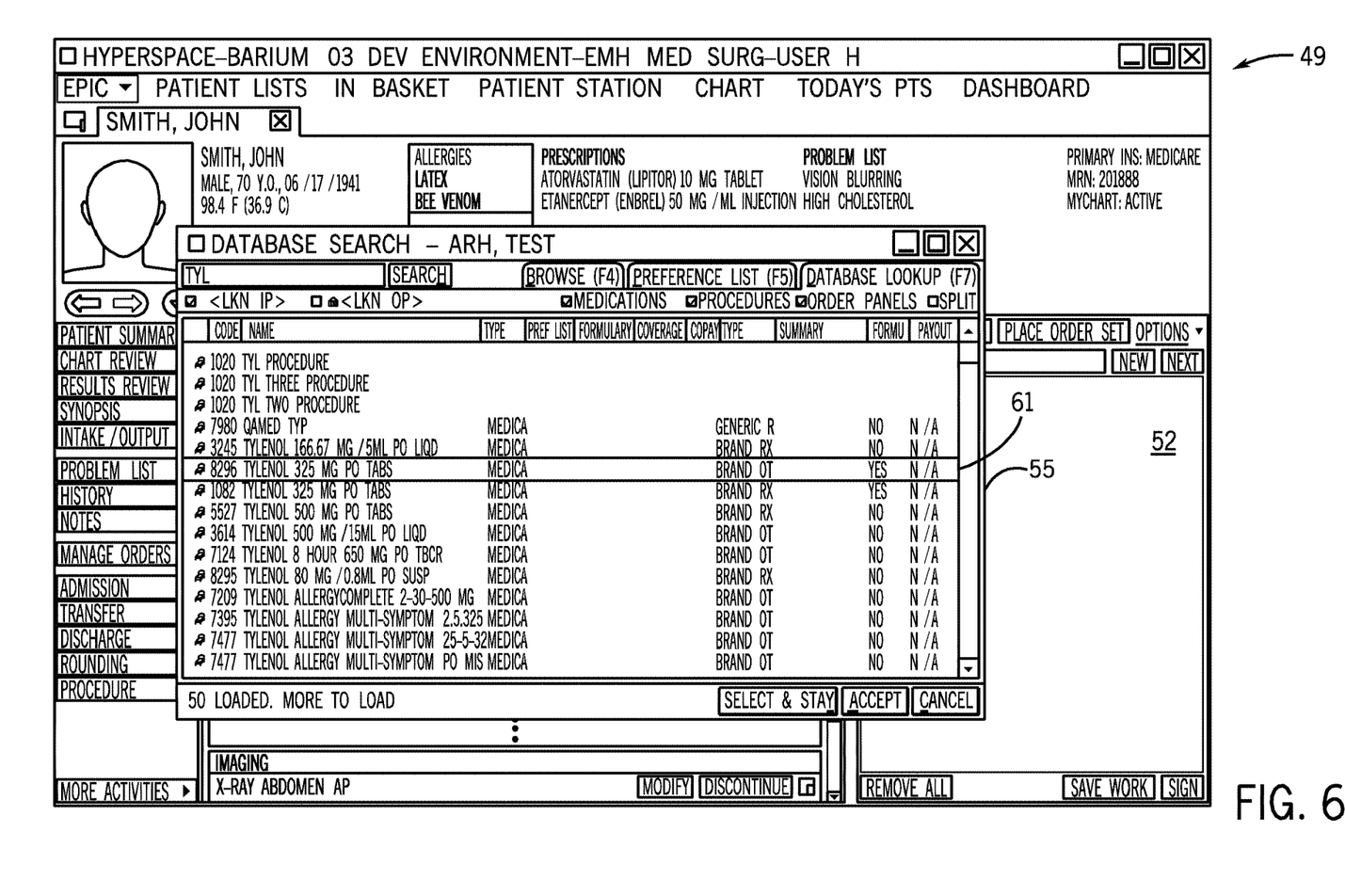
FIG. 6 is an illustration of an exemplary screen for medical order data entry and comparison during entry of a new medical order.
Figure 9:
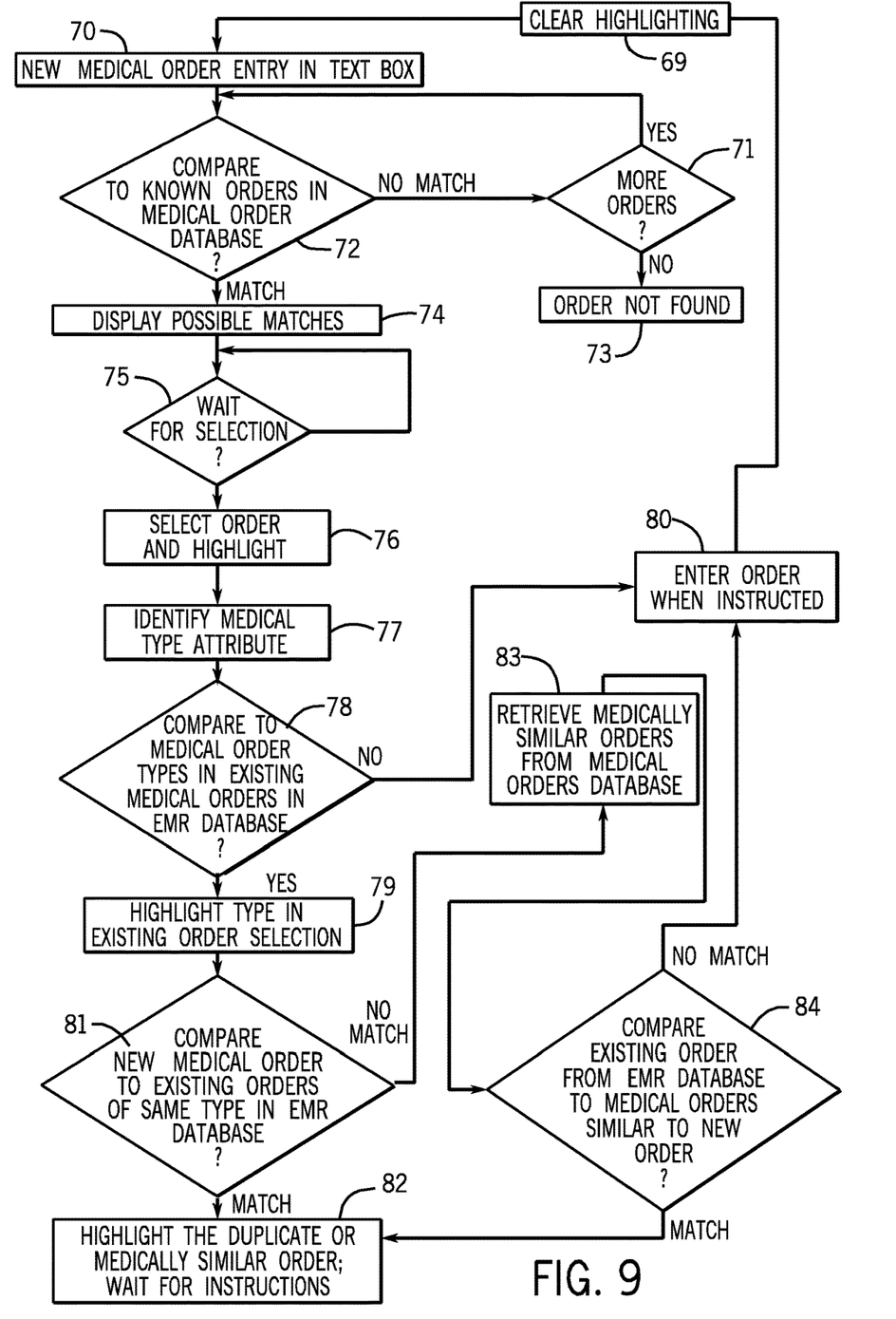
FIG. 9 is a flow chart illustrating one embodiment of a comparative analysis for identifying medically similar medical orders in accordance with the present invention.
Figure 10:
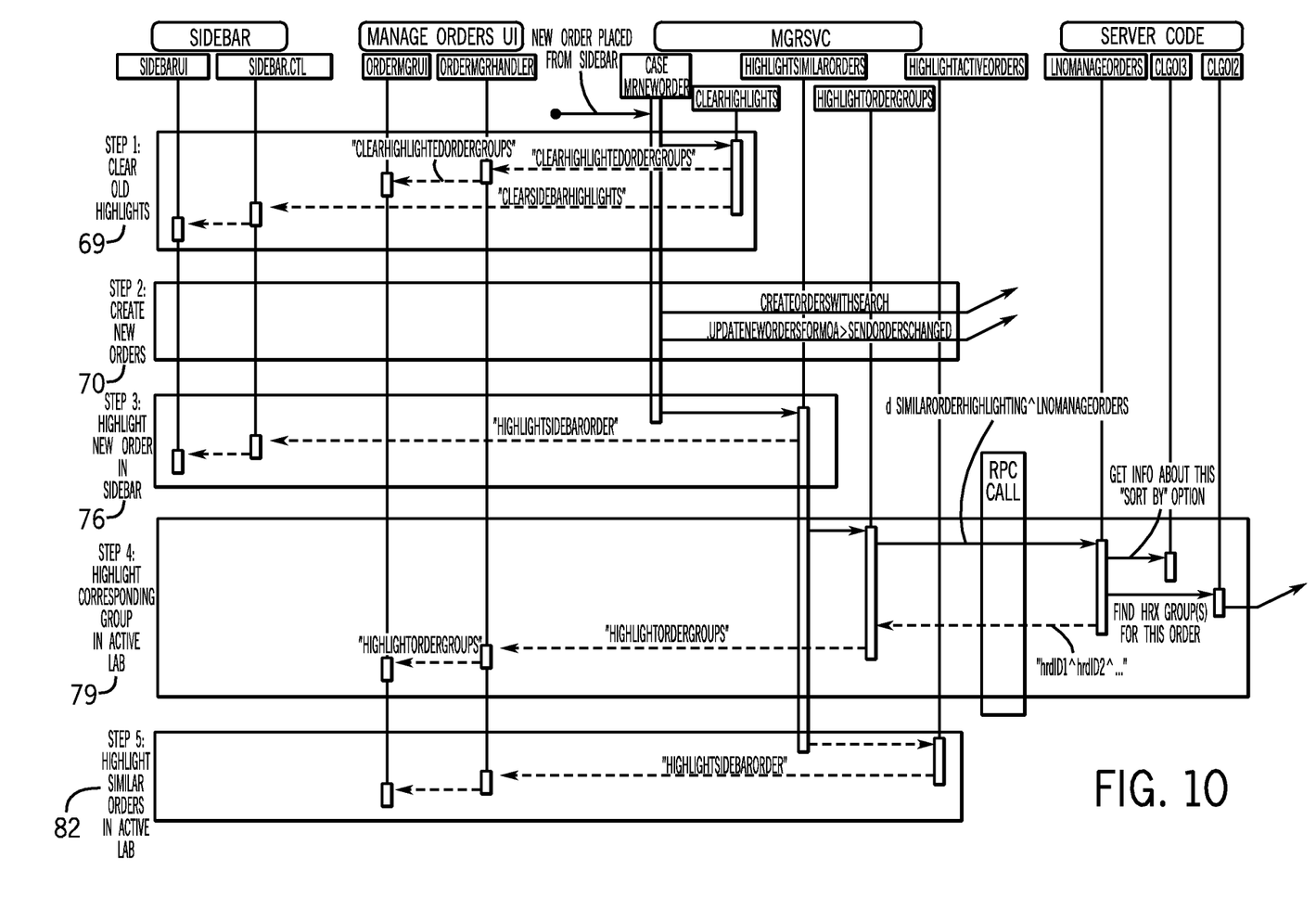
FIG. 10 is a sequence diagram illustrating the process of identifying and highlighting medically similar orders.

Referring still to FIG. 5, and now also to FIGS. 4 and 9, in the first step of the process, any existing highlighting is cleared (step 69). As the new order is entered into text box 54 (step 70), the processor 20 compares the entered text to known orders 44 in a medical order database 40 (step 72) until all possible matching orders are identified (step 74). The processor 20 can, for example, parse the entered text string and compare either the entire text string or portions of the text string to known orders 44. Rules can be provided specifying the degree of similarity between the text string or text string portion and a known order 44 to trigger identification as a possible match. The processor 20 can then display possible matches (step 74) to the medical practitioner. Referring now also to FIG. 6, the matches can be displayed in a pop-up window or screen 55. The medical practitioner can use a mouse, arrow keys, or other user input device to highlight and select an entry 61. As shown here in FIGS. 5 and 6, for example, when a medical practitioner enters the letters TYL (FIG. 5), a series of orders generated by the rules and including these letters is provided in window 55 for selection by the user (FIG. 6).

Alternatively, the medical practitioner can continue to enter data directly into the text box 54, using the window 55 as a guide, for example. If the practitioner chooses to enter the medical order into the new order entry text box 54 rather than selecting an order from the window 55, and the order is not found, the process can be stopped and, for example, an error notice can be communicated to the medical practitioner on the display 22, indicating that the new order entry was not found in the database 40 (step 73). In some applications, a spell check can be performed on the new entry, and alternative choices offered to the medical practitioner.

In either case, the processor 20 waits (step 75; FIG. 9) until the user selects an order from the list, or completely types the order into the text box 54. When the entry is complete, the user can activate a "new" button, key or icon 53, activate the enter key, or use a mouse or other device from user interface 22 to indicate acceptance of the entry, or otherwise provide an indication to the processor that an order entry has been identified and is ready for review and comparison for medically similar orders (step 76).

Figure 7:
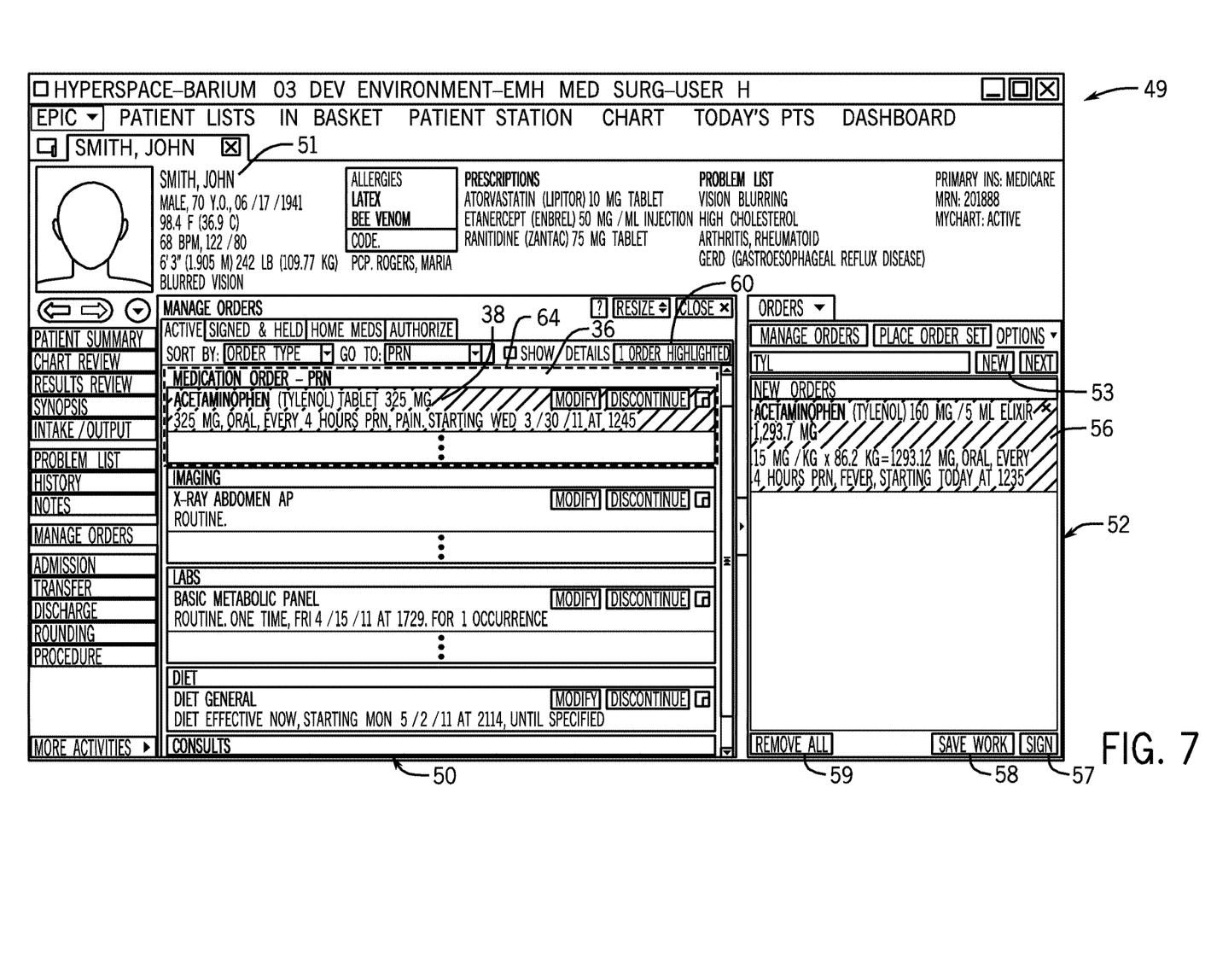
FIG. 7 is an illustration of an exemplary screen for medical order data entry and comparison after entry of a new medical order.

Referring now to FIG. 7, when an order is selected, the selected new medical order 56 is displayed and highlighted in the new order section 52. Referring again to FIG. 9, the processor 20 in computer 12 takes a series of steps to evaluate the new medical order 56 to determine whether the new medical order 56 is medically similar to any of the existing medical orders 38 for the patient in database 30, and to provide an indicator to the medical practitioner when a medically similar order may have been made. After the processor 26 receives the indicator that the new order 56 has been selected (step 76), the processor 20 first identifies the medical order type attribute (step 77).

The processor 20 then compares the medical order type or types 42 identified in database 40 as corresponding to the new order 56 to each of the medical order types 36 corresponding to the existing orders 38 in the patient database 30 (FIG. 3) (step 78). As described above, where CPT codes are used, this analysis can include a comparison to medical orders that have a CPT code within a predetermined numerical range of the CPT code corresponding to the new medical order 56. If no match is found, no medical orders of the corresponding medical order type have been previously made, and the order can be entered when the medical practitioner indicates entry by, for example, activating the "sign" button 57. (Step 80) In some applications, the highlighting of the new medical order 56 could be changed or adjusted to indicate that no similar orders or duplicates have been found, providing an indicator to the medical practitioner that the order can be completed without overlap or duplication.

If the database 30 includes existing medical orders 38 of the same medical order type 36 as the new medical order 56, the processor 20 highlights the order type 36 in the existing order section 50 of the display 22 (step 79). As shown in FIG. 7, the existing orders 38 of the same or closest medical order type 36 are scrolled to the top of the existing order section 50 of the display 22 and highlighted, drawing the attention of the medical practitioner to the relevant group of existing orders in existing order section 50. The processor 20 compares the new medical order 56 to the existing medical orders 38 corresponding to the identified medical order type, initially to determine whether an exact match, or duplicate, exists in the existing order database 30. (step 81). If a match is found, the processor 20 can highlight the corresponding medical order type in existing order section 50 of the screen 49 (step 82) to provide a visual indicator to the medical practitioner that a duplicate exists. The new medical order 56 can also be highlighted. As shown here, for example, a line or box 64 can be drawn around the orders corresponding to each of the medication order—PRN medical orders, allowing the medical practitioner to easily identify the existing orders of this type.

Referring still to FIG. 7, if no identical match is found, the processor 20 retrieves similar orders from the medical orders database (step 83) and compares the similar medical orders 46 corresponding to the new medical order 56 in database 40 to the existing orders 38 of the same medical order type or types in database 30 (step 84). As described above, the similar medical orders 46 are orders that may be medically similar to the new medical order, rendering the new order unnecessary or repetitive. If a match is found, the processor 20 can, again, highlight the corresponding existing medical order 38 in existing order section 50 of the screen 49 (step 82), and also the new medical order 56 in order entry section 52, to provide a visual indicator to the medical practitioner that further analysis is required before completing the order. Since more than one medical order may be similar to the existing order, this process can be repeated until all of the similar medical orders are identified, and can also be provided after a duplicate medical order is identified. Additionally, the medical order database 40 can store a probability or confidence factor, indicating a degree of similarity between corresponding similar types of medical orders, and this confidence factor can be used in providing feedback to the medical practitioners initiating the order, as described below.

If no match is found, the new order 56 is not medically similar to any existing orders, and the new order 56 can be entered into the patient database 30. (Step 80) In one embodiment of the invention, the medical practitioner can save the order entries by activating the "save work" button 58, and sign the order by activating the "sign" button 57. When the new order is saved, and the order is signed, the order is stored in the patient database 30, with the corresponding medical order type. If the medical practitioner instead decides not to enter the order, the medical practitioner can activate the "remove" button 59, removing the order from screen. If no match is found, the processor may also perform a spell check to determine if the order was entered correctly, or provide the medical practitioner with a number of alternate entries that the user may have intended to type. Alternatively, the processor 20 may provide a pop-up window, highlight the entry, or provide another indicator to the medical practitioner that no matches were found, or that the order entry may be incorrect. The user can then delete the order, save the order, or change the order and re-start the process.

Referring again to FIG. 7, an example of the application of the order entry steps and review process described above can be seen by reference to the display 49. As shown here, a medical practitioner has entered a new order 56 for acetaminophen in the new order section 52 of the display screen 49. In response to this entry, the system 10 evaluates the new order entry 56 to determine the corresponding medical order type or types 42, as discussed above with reference to FIG. 7. When a match is found, the system can scroll or sort the existing order section 50 of the display 49 to align the medical order type 36 at the existing entry 38 corresponding to the new entry adjacent the new order entry 56 at the top of the screen 49, thereby allowing medical personnel to easily view the possible medically similar order. In the example shown here, the corresponding entry corresponds to the medication order—PRN medical order type 42, and this category is scrolled to the top of the existing order section 50 near the new order entry 56. The corresponding medical order type 42 is visually highlighted on the screen 49 by, for example, drawing a highlighting line 64 around the identified order type and each of the corresponding orders in that particular portion of the screen 49. A highlight, here shown as cross-hatching, can also be provided on the existing medical order 38 for acetaminophen which has already been initiated for the patient. The new order entry 56 in new order entry section 52 can also be similarly highlighted. The medical practitioner is therefore visually notified that a duplicate order exists in the medical order type selected. Because the duplicate order is scrolled to a location where it can be easily seen, the person entering the order can view the information easily and determine whether to change the existing order, delete the new order, or make a different recommendation, thereby minimizing the possibility of a duplicate or similar entry. Although cross-hatching and dotted lines are shown here for highlighting, changes in color, bold fonts, italics, and other types of highlighting can be used as described more fully below.

Figure 8:
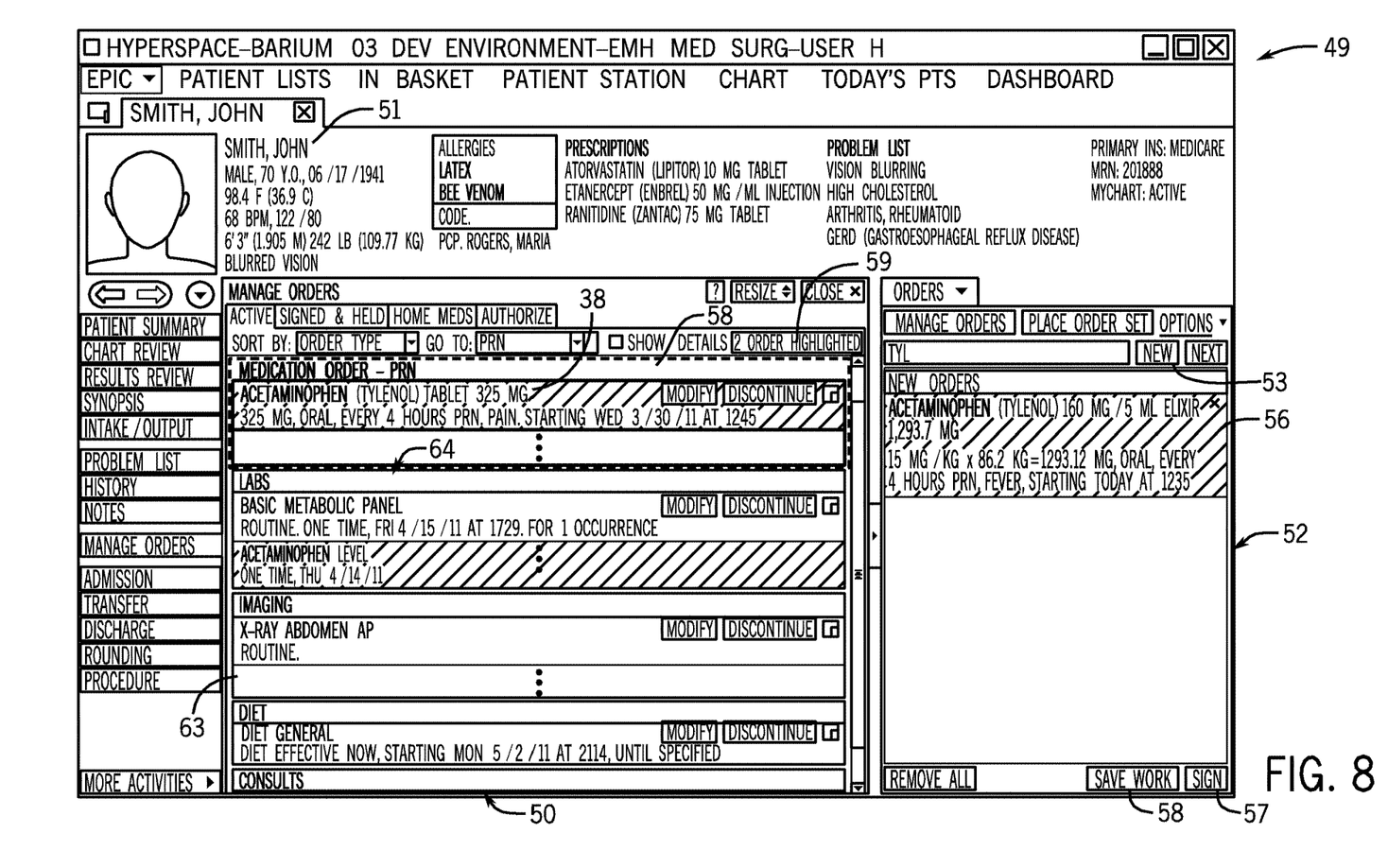
FIG. 8 is an illustration of an exemplary screen for medical order data entry and comparison illustrating highlighting of two medically similar orders.

Referring now to FIG. 8, either in addition to the steps described above, or as an alternative to the steps described above, the processor 20 can also search for medically similar orders 46 of any medical order type 42. Using similar methodology to that described above, the processor 20 can, for example, search all existing medical orders 38 for orders that are medically similar to the new medical order 56. Here, for example, the new medical order 56 includes "acetaminophen." Acetaminophen level testing has been ordered for the patient as part of the "lab" medical order type group. Here, the processor identifies the use of the term "acetaminophen" in the lab type, and flags this order as medically similar. As shown in FIG. 8, the "labs" medical order type containing the medically similar order can be scrolled up on the screen 49, and the term "acetaminophen" highlighted to indicate to the medical practitioner that the acetaminophen level test is a medically similar or overlapping order. The "labs" medical order type can be highlighted, as described above, or, since this order type does not match the order type attribute of the new medical order 56, may be left un-highlighted. Multiple medically similar orders can therefore be highlighted in the existing medical order section 50 of the display 22. A count of the number of medically similar orders can be provided in, for example, a text box 60 for the medical practitioner. These medically similar orders also can be organized based on degree of similarity. Here, for example, the first highlighted order includes both the same medical order type attribute and a medically similar order. The next group includes a medically similar order, but does not have the same medical order type attribute. Various methods for determining degree of similarity can be used in ordering the display. The degree of similarity can be indicated by order of display, as shown here, by the color of text, or using other variations in the highlighting options.

Although a specific method of highlighting duplicate entries has been described, various highlighting methods can be used that would fall under the scope of the invention. For example, in some applications, the duplicate or similar entries could be emphasized by changing the font and displaying either the duplicate entry or both the newly entered and duplicate entries in an emphasized font, such as italics, bold, or underline. Alternatively, the size or color of the font of the entries could be adjusted to emphasize the match. In other alternatives, an icon or other visual indicator could be provided near the duplicate or medically similar entry, near the new medical order, or both.

In another example, a color coded system can also be used to identify various grades of similarity. For example, if a known duplicate order is found, the duplicate orders can be displayed in red, indicating a very likely need to stop and re-evaluate the situation before completing the order. Where a similar order is substantially medically similar to an existing order, such as, for example, where a generic drug is ordered at the same time as a brand name drug, these entries can be highlighted in orange. As discussed above, a confidence factor indicating a likelihood that two orders are similar can also be provided in the medical orders database 40, and this data can be used to vary the colors of the highlighting, varying, for example, from yellow to orange, to red, depending on the degree of confidence. Similarly, a "green" highlight could be used to indicate that no duplicate or similar order has been found, and the entry of the order can proceed. In situations where more than one duplicate or similar order has been identified, the identified existing orders could be color-coded depending on the degree of similarity. Similarly, the size of the font could be varied, with the largest font being used to display the closest similar order, and less similar orders can be displayed using a smaller, but still emphasized, font. The similar orders could also be sorted based on degree of confidence, and displayed in the sorted order, displayed with a numerical ranking, or displayed with a confidence factor rating.

Various other types of visual indicators could also be used. For example, the duplicate orders could be highlighted by causing the corresponding orders to "blink" on and off. Icons can be used to identify duplicate and similar orders, and can be positioned adjacent the entries for analysis. The icons could also be used to provide selective access to information about the highlighted order, and information about why the highlighted order is considered to be similar to the new order entry. This information could be used by the medical practitioners to make a determination regarding whether to proceed with an order.

In addition to visual highlighting, an audible warning could be used to indicate that a duplicate or similar entry has been identified. Again, the audible warnings could be varied depending on the degree of confidence that an order needs to be re-evaluated before entry, and range in intensity or volume depending on the correlation factor.

Although a specific method and series of steps for identifying duplicate or similar orders has been described above, this method is exemplary. Various other methods can be also be used. For example, in some applications, such as the process described above with reference to FIG. 8, the processor can identify and highlight all of the orders of the same medical order type in the existing medical order section of the display without searching for an exact duplicate or similar order, and thereby allow the medical practitioner to evaluate all of the corresponding orders. In some applications, all orders having a similar spelling could be highlighted, and preferably sorted to the top of the screen, thereby allowing a medical practitioner to easily review the data for possible errors.

Additionally, although the system is described as providing medical orders categorized in medical order types, the comparison could be made to each medical order rather than the medical order types. Various other methods of evaluating medically similar orders and methods for categorizing medical orders and medical order types can also be used. Further, although the medical practitioner enters the medical order into the system in the method described above, and the system automatically determines the medical order type, in alternate embodiments the medical practitioner could enter both the new medical order type and the new medical order.

In some applications, the amount and type of feedback provided to the user can be varied based on, for example, the identity of the medical practitioner accessing the system. For example, selective access can be provided to the system using password protection, biometric data, RFID codes, barcodes, or other types of identification systems, and the amount of feedback provided could be varied based on the identity of the medical practitioner accessing the system. A first user could, for example, request that feedback be provided only when an exact duplicate is found. A second user could request that all similar orders be identified. A third user could request that all orders of the corresponding medical order type be highlighted. In some applications, a facility could implement a policy that various categories of employees be provided with selected types of feedback. For example, a facility could provide a certain level of feedback to all physicians, and a different level of feedback to physician assistants or nurse practitioners.

Furthermore, although the duplicate identification process is described as controlled by processor 20 of computer 12, it will be apparent to one of ordinary skill in the art that the process could be performed by other computer devices in the network as well. Additionally, although data entry is described by keyboard entry through a text box, it will be apparent that data can be entered using a pen-based system, through voice commands, through drop down boxes, by scanning data into the computer, or through other methods known to those of skill in the art.

It should be understood that the methods and apparatuses described above are only exemplary and do not limit the scope of the invention, and that various modifications could be made by those skilled in the art that would fall under the scope of the invention. To apprise the public of the scope of this invention, the following claims are made:

We claim:

1. A medical records computer system, the system comprising:

a processor;

a memory coupled to the processor, the memory storing a medical orders database, the medical orders database comprising a plurality of known medical orders grouped in a plurality of categories based on a medical order type, the plurality of medical order type categories selected to define a medical similarity between medical orders that fall within the corresponding category based on at least one of current procedural terminology ("CPT") codes, International Classification of Diseases, Ninth Revision, ("IC-9") database and International Classification of Diseases, tenth Revision, ("IC-10") database; and a patient database comprising a plurality of existing medical orders initiated for a selected patient, each of the plurality of existing medical orders categorized in a medical order type;

a user interface device coupled to the processor; and a display communicatively coupled to the processor and the memory, the display including an existing order portion displaying at least one existing medical order in a first column, and a new order portion adjacent the existing order portion in a second column for simultaneously displaying a new medical order entered by medical personnel and the at least one existing medical order, the processor being programmed to:

receive at least a portion of a new medical order through the user interface device in a text box and display the at least a portion of the new medical order on the new order portion;

compare the at least a portion of the new medical order to a database of known medical orders as the at least a portion of the new medical order is entered through the user interface, and providing a list of corresponding known medical orders for the user to select;

receive a selected known medical order and compare the selected known medical order to the medical orders database to categorize the selected known medical order in a medical order type;

compare the selected known medical order to the plurality of existing medical orders of the same medical order type in the patient database to determine whether at least one of the plurality of existing medical orders is a duplicate of the new medical order and to determine whether the at least one of the plurality of existing medical orders is a medically similar order that is not a duplicate of the new medical order; and upon determining that at least one of the plurality of existing medical orders is a duplicate of the new medical order or is a medically similar order that is not a duplicate of the new medical order, scrolling the existing medical order portion of the display to position the identified duplicate of the new medical order or medically similar order that is not a duplicate of the new medical order to a top of the first column adjacent the new medical order in the second column to highlight the at least one existing medical order and the new medical order on the display, wherein a medical practitioner entering the new order is provided with a notification to evaluate the at least one existing medical order and the new medical order; and preventing entry of the new medical order into a patient database until the new medical order is authorized by a medical practitioner.

2. The medical record computer system as recited in claim 1, wherein the existing order portion of the display displays a plurality of existing medical orders categorized in medical order types, and wherein the processor is further programmed to highlight at least one of the predetermined medical order types that contains the existing medical order that is medically similar to the new order.

3. The medical records computer system as recited in claim 1, wherein the processor is programmed to highlight at least one of the existing medical order and the new medical order on the display by changing a font of at least one of the existing medical order and the new medical order.

4. The medical records computer system as recited in claim 1, wherein the processor is programmed to highlight at least one of the existing medical order and the new medical order on the display by changing a color of a font of at least one of the existing medical order and the new medical order.

5. The medical records computer system as recited in claim 1, wherein the processor is programmed to highlight at least one of the existing medical order and the new medical order on the display by enclosing the at least one of the existing medical order and the new order with a line on the display.

6. The medical records computer system as recited in claim 1, wherein the processor is programmed to highlight at least one of the existing medical order and the new medical order by producing an audible warning sound when the processor determines that the existing medical order is medically equivalent to the new medical order.

7. The medical computer records system as recited in claim 1, wherein the processor is programmed to highlight at least one of the existing medical order and the new medical order by sorting the existing medical orders in the existing medical order portion of the display to position the existing medical order at a position adjacent the medically similar new medical order in the new medical order portion of the display.

8. The medical records computer system as recited in claim 1, wherein the memory further comprises a database storing a plurality of known medical orders and correlating these orders to medically similar orders, and the processor is further programmed to:

compare the known medical orders to the new medical order to identify a match;

retrieve the corresponding medically similar medical orders from the database;

compare the medically similar orders to the existing medical order to determine whether the new medical order is similar to the existing medical order; and highlight the existing medical order when it is medically similar to the new medical order wherein a notification is provided.

9. The medical records computer system as recited in claim 8, wherein the database storing a plurality of known medical orders further correlates the known medical orders with categories of medical order types, the existing medical orders are correlated with corresponding medical order types on the display, and the processor is further programmed to highlight the medical order type corresponding to the new medical order on the existing order portion of the display.

10. A method for minimizing entries of medically similar orders by medical personnel in a computerized medical records system, the method comprising the following steps:

storing at least one existing medical order initiated by medical personnel for a specific patient, and displaying the existing medical order on a first portion of a display screen in a first window;

categorizing the at least one existing medical order as one of a plurality of medical order type categories, the plurality of medical order type categories selected to define a medical similarity between medical orders that fall within the corresponding category based on at least one of current procedural terminology ("CPT") codes, International Classification of Diseases, Ninth Revision, ("IC-9") database and International Classification of Diseases, tenth Revision, ("IC-10") database;

receiving a new medical order for the patient through a user interface including a text box, and simultaneously displaying the new medical order on a second portion of the display screen in a second window;

using a processor to determine the medical order type of the new medical order, and to compare the medical order type of the new medical order to the medical order type of the at least one existing medical order;

highlighting the medical order type of the at least one existing medical order that is medically similar to the new medical order to provide a notification to a user that a medically similar order has been entered into the text box by scrolling the medical order type that is medically similar to a top of the first window; and comparing the new medical order to the existing medical orders corresponding to the identified medical order type to identify either a duplicate order or a medically similar order that is not a duplicate; and highlighting the medical order identified as a duplicate or a medically similar order; and entering the new medical order into a database when authorization is received from a medical practitioner.

11. The method as recited in claim 10, wherein the steps of identifying a medically similar order further comprises the steps of:

storing a plurality of known medical orders and corresponding medically similar orders in a database for comparison;

comparing the known medical orders to the new medical order to identify a match;

retrieving the corresponding medically similar orders;

comparing the medically similar orders to the existing medical order to determine whether the new medical order is medically similar to the existing medical order; and highlighting the existing medical order when it is medically similar to the new medical order.

12. The method as recited in claim 10, further comprising the step of comparing at least a portion of the new medical order to a database of known medical orders as the medical order is entered through the user interface, and providing a list of corresponding known medical orders for the user to select.

13. The method as recited in claim 12, further comprising the step of providing one or more alternatives for the user to select as the new medical order is entered.

14. The method as recited in claim 10, further comprising the step of highlighting at least one of the existing medical order and the new medical order to provide a notification happens in real time.

15. A medical records computer system, the system comprising:

a processor;

a memory coupled to the processor, the memory storing:

a medical orders database, the medical orders database comprising a plurality of known medical orders grouped in a plurality of categories based on a medical order type, the plurality of medical order type categories selected to define a medical similarity between medical orders that fall within the corresponding category based on at least one of current procedural terminology ("CPT") codes, International Classification of Diseases, Ninth Revision, ("IC-9") database, and International Classification of Diseases, tenth Revision, ("IC-10") database; and a patient database comprising at least one existing medical order initiated for a selected patient, the existing medical order categorized in a medical order type;

a user interface device coupled to the processor; and a display communicatively coupled to the processor and the memory, the display including an existing order portion in a first window for displaying at least one existing medical order, and a new order portion in a second window for displaying a new medical order entered by medical personnel, the processor being programmed to:

receive a new medical order entered through the user interface device and displayed on the new order portion;

compare the new medical order to the orders database to determine a medical order type;

compare the new medical order to the existing medical orders of the same medical order type to determine whether the at least one existing medical order is medically similar to the new medical order;

upon determining that the new medical order is medically similar to the at least one existing medical order in the patient database, scrolling the at least one existing medical order that is medically similar to a top of the first window; and highlight at least one of the existing medical order type corresponding to the new medical order, the existing medical order that is medically similar to the new medical order, and the new medical order on the display when the existing medical order is medically similar to the new medical order, wherein a medical practitioner entering the new order is provided with a visual notification;

preventing entry of the new medical order into the patient database until the new medical order is authorized by a medical practitioner.

16. The medical record computer system as recited in claim 15, wherein the existing order portion of the display displays a plurality of existing medical orders categorized in medical order types, and wherein the processor is further programmed to highlight at least one of the predetermined medical order types that contains the existing medical order that is medically similar to the new order.

17. The medical records computer system as recited in claim 15, wherein the medical order database further includes a plurality of predetermined medically similar orders that correspond to a known medical order, and the processor is programmed to evaluate the medically similar orders, and to highlight the at least one existing medical order or the new medical order on the display when the processor determines that the existing medical order is medically similar to the new medical order.

18. The medical records computer system as recited in claim 15, wherein the processor is programmed to group the existing medical order with at least one other existing medical order of the same medical order type on the display, and to highlight the medical order type that corresponds to the new medical order in the existing order portion of the display when a medically similar or duplicate order is found.

19. The medical records computer system as recited in claim 18, wherein the processor is further programmed to scroll the medical order type corresponding to the new medical order to a top portion of the existing order portion of the display to highlight the medically similar entry.

20. The medical records computer system as recited in claim 18, further comprising the step of visually grouping the existing medical orders corresponding to a medical order type by enclosing the existing medical orders in a display box in the existing order portion of the display.

21. The medical records computer system as recited in claim 15, wherein the processor is programmed to highlight at least one of the existing medical order and the new medical order on the display by scrolling the display to position the existing medical order and the new medical order adjacent one another in the first and second portions of the display.

22. The medical computer records system as recited in claim 15, wherein the processor is programmed to highlight at least one of the existing medical order and the new medical order by sorting the existing medical orders to position the existing medical order at a position adjacent the new medical order.

23. The medical computer records system as recited in claim 15, wherein the processor is further programmed to highlight existing medical orders of the same medical order type as the new medical order to allow a medical practitioner to compare the new medical order to existing medical orders.

24. The medical computer records system as recited in claim 15, wherein the medical order type corresponds to a predetermined range of CPT codes.

25. The medical computer records system as recited in claim 15, wherein the medical order database includes a standardized listing of medical order types.

\* \* \* \* \*